US008455264B2

(12) United States Patent
Russell et al.

(10) Patent No.: US 8,455,264 B2
(45) Date of Patent: Jun. 4, 2013

(54) FLUORESCENCE BASED DETECTION OF SUBSTANCES

(75) Inventors: David Russell, Runhall (GB); Richard Leggett, Ware (GB); Emma Lee-Smith, Stalham (GB); Sue Jickells, Longham (GB); Barbara Daniel, London (GB)

(73) Assignee: Intelligent Fingerprinting Limited, Norwich (GB)

( * ) Notice: Subject to any disclaimer, the term of this patent is extended or adjusted under 35 U.S.C. 154(b) by 967 days.

(21) Appl. No.: 12/294,276

(22) PCT Filed: Mar. 23, 2007

(86) PCT No.: PCT/GB2007/001059
§ 371 (c)(1),
(2), (4) Date: May 1, 2009

(87) PCT Pub. No.: WO2007/110605
PCT Pub. Date: Oct. 4, 2007

(65) Prior Publication Data
US 2009/0230322 A1    Sep. 17, 2009

(30) Foreign Application Priority Data

Mar. 24, 2006  (GB) .................................. 0605965.3

(51) Int. Cl.
*G01N 33/553*   (2006.01)
*G01N 33/53*    (2006.01)

(52) U.S. Cl.
USPC ............................ 436/525; 436/526; 435/7.1

(58) Field of Classification Search
USPC .................... 436/525, 526; 435/7.1
See application file for complete search history.

(56) References Cited

U.S. PATENT DOCUMENTS

| 5,244,815 A | 9/1993 | Guirguis |
| 6,165,798 A * | 12/2000 | Brooks .......................... 436/169 |

(Continued)

FOREIGN PATENT DOCUMENTS

| EP | 324040 | 7/2003 |
| JP | 60-222033 A | 11/1985 |

(Continued)

OTHER PUBLICATIONS

Powell Tremaine et al: "Fluorescent biorecognition of gold nanoparticle¬lgG conjugates self-assembled on e-beam patterns" Biotechnology Progress, vol. 22, No. 1, Jan. 2006, pp. 106-110, XPO02440396ISSN: 8756-7938.

(Continued)

*Primary Examiner* — Mark Shibuya
*Assistant Examiner* — Pensee Do
(74) *Attorney, Agent, or Firm* — Lando & Anastasi, LLP (57) ABSTRACT

A method for the fluorescent detection of a substance, the method comprising providing particles comprising a metal or a metal oxide core, wherein one or more optionally fluorescently tagged antibodies or human specific peptide nucleic acid (PNA) oligomers for binding to a substance is/are bound, directly or indirectly, to the surface of the metal or metal oxide; contacting a substrate, which may or may not have the substance on its surface, with the particles for a time sufficient to allow the antibody/PNA oligomer to bind with the substance; removing those particles which have not bound to the substrate; if the antibodies or PNA oligomers are not fluorescently tagged, contacting the substrate with one or more fluorophores that selectively bind with the antibody and/or substance, then optionally washing the substrate to remove unbound fluorophores; and illuminating the substrate with appropriate radiation to show the fluorophores on the substrate.

14 Claims, 7 Drawing Sheets

U.S. PATENT DOCUMENTS

| | | | | |
|---|---|---|---|---|
| 2002/0127574 | A1* | 9/2002 | Mirkin et al. | 435/6 |
| 2002/0192841 | A1* | 12/2002 | Kojima | 436/518 |
| 2003/0059850 | A1* | 3/2003 | Evans | 435/7.1 |
| 2004/0219361 | A1* | 11/2004 | Cui et al. | 428/402.2 |
| 2005/0260766 | A1 | 11/2005 | Paul et al. | |

FOREIGN PATENT DOCUMENTS

| | | |
|---|---|---|
| JP | 05-240858 A | 9/1993 |
| JP | 07-151726 A | 6/1995 |
| JP | 2000074920 A | 3/2000 |
| JP | 2004-149507 A | 5/2004 |
| JP | 2005-520125 A | 7/2005 |
| JP | 2011-507516 A | 3/2011 |
| WO | 0194947 A1 | 12/2001 |
| WO | 2005019824 | 3/2005 |
| WO | 2005066632 A1 | 7/2005 |

OTHER PUBLICATIONS

Takizawa Toshihiro et al: "FluoroNanogold is a bifunctional immunoprobe for correlative fluorescence and electron microscopy" Journal of Histochemistry and Cytochemistry, vol. 48, No. 4, Apr. 2000, pp. 481-485, XPO024403971SSN: 0022-1554.

Hainfelo J F et al: "New frontiers in gold labeling" Journal of Histochemistry and Cytochemistry, Histochemical Society, New York, NY, US, vol. 48, No. 4, Apr. 2000, pp. 471-480, XPO02368643 ISSN: 0022-1554.

Demers L M et al: "A Fluorescence-Based Method for Determining the Surface Coverage and Hybridization Efficiency of Thiol-Capped Oligonucleotides Bound to Gold Thin Films and Nanoparticles" Analytical Chemistry, American Chemical Society. Columbus, US, vol. 72, No. 22, Nov. 15, 2000, pp. 5535-5541, XPO01204824 ISSN: 0003-2700.

Campas et al: "Characterisation and determination of stability and functionality of biofunctionalised colloidal , gold nanoparticles" AnalYtica Chim!Ca Acta, Elsevier, Amsterdam, NL, vol. 556, No. 2, Jan. 25, 2006, pp. 306-312, XPO05236650 ISSN: 0003-2670.

Nguyen Thi Kim Thanh et al: "Development of an Aggrega Tion¬BASED Immunoassay for Anti-Protein A Using Gold Nanoparticles" Analytical Chemistry, American Chemical Society. Columbus, US, vol. 74, No. 7, Apr. 1, 2002, pp. 1624-1628, XPOO 1115850 ISSN: 0003-2700.

Ferretti S et al: "Self-assembled mono layers: a versatile tool for the formulation of bio-surfaces" TRAC, Trends in Analytical Chemistry, Elsevier, Amsterdam, NL, vol. 19 No. 9, Sep. 2000, pp. 530-540, XPO04209450 ISSN: 0165-9936.

Hone, D., Haines, A, Russell, D.: "Rapid, quantative colorimetric detection of a lectin using man nose stabilized gold nanoparticles" Langmuir, vol. 19, Mar. 7, 2003, pp. 7141-7144, XPO02440398.

Villal Ta Danila et al: "Analytical and diagnostic accuracy of the EliA (TM) automated enzyme fluoroimmunoassay for antineutrophil cytoplasmic autoantibody detection" Clinical Chemistry and Laboratory Medicine, vol. 42, No. 10, 2004, pp. 1161-1167, XPO09092148 ISSN: 1434-6621.

International Search Report for corresponding Application No. PCT/GB2007/001059 mailed Oct. 14, 2008.

Simonite, Tom. 'Fingerprints Reveal Clues to Suspect's Habits' New Scientist Tech. News Service. Apr. 3, 2006. www.newscientisttech.com.

Lin et al. "Determination of ABO Blood Types from Fingerprints Using Immunohistochemical Method". Legal Medicine, Japan, Japanese Society of Legal Medicine, Apr. 10, 1993. vol. 47, No. 2, p. 98-107.

Miura et al. "Preparation of Gold Nanoparticles and Their Applications for Biosensing". Dojin News, No. 113, Japan, Feb. 8, 2005.

* cited by examiner

FLUORESCENCE BASED DETECTION OF SUBSTANCES

This application is a national stage application under 35 U.S.C. §371 of PCT/GB2007/001059 filed on Mar. 23, 2007. PCT/GB2007/001059 claims priority to GB 0605965.3 filed on Mar. 24, 2006.

The present invention relates to the detection of substances, including, but not limited to, biological substances, drugs and/or metabolites, using fluorescence. The present invention may be used to detect the presence of certain compounds in substances excreted by humans, e.g. in a fingerprint left on a substrate, or the bodily fluid itself e.g. blood, saliva, semen.

Forensic scientists often find fingerprints and biological substances at the scene of a crime. Currently, forensic examiners initially search for signs of blood, semen and saliva with the naked eye. This is followed by examination using specialised light sources. Semen and saliva exhibit fluorescence under some, but by no means all, circumstances. Blood has no native fluorescence but does have a strong absorption band centred around 415 nm. Hence it can be 'visualised' under light sources as a dark spot against a lighter background. This does not work on many substrates, and/or when minute spots of blood are present or when the perpetrator of a crime has tried to clean-up traces. Where visual and light source inspection has failed to indicate the presence of body fluids, scene examiners rely on submission of 'best estimate' evidence, submitting items for further examination which they think may be a source of DNA (e.g. underwear, cigarette butts etc.). These approaches often fail to detect traces of body fluids. Even if visual or light source examination has revealed what may be blood, semen or saliva, this is presumptive and further calorimetric and, in the case of presumptive semen, microscopical tests are required to confirm the presence of the various fluids. A separate test is required for each body fluid, with different procedures and reagents used for each. There is thus a desire to create a test which can more readily detect one or more substances that may derive from a human, such as saliva, blood, semen and metabolites.

Fingerprint identification is one of the cornerstones of forensic evidence. However, currently a fingerprint is useful solely when police or other security agencies are able to obtain a positive match with those prints present on databases.

When visualised under a microscope, the skin on the palms and fingers appear as ridges and grooves. It is the pattern of these friction skin ridges that produces the unique fingerprint. Each skin ridge has a single row of pores, through which sweat is excreted and deposited on the surface of the skin. When a finger touches a surface, sweat is deposited leaving an impression of the finger's ridge pattern, referred to as a latent fingerprint. Such fingerprints are considered 'invisible prints' as they require physical or chemical treatments to enable visualisation.

Sweat is the ultrafiltrate of blood plasma, containing inorganic ions, lactate, urea and amino acids and these species are therefore present within a freshly deposited fingerprint. In addition, it is known that orally ingested and metabolised drugs are excreted in sweat. These drugs have been measured in sweat through the use of collection devices, such as patches of adsorbent cotton, followed by extraction and subsequent analysis using techniques such as gas chromatography coupled with mass spectrometry (GC-MS) detection. However, the methods are laborious, require a large amount of sweat collected over a period of time and are therefore not suitable for rapid analysis, for example roadside testing of persons suspected of driving under the influence of drugs. The detection of substances in fingerprints has not been possible using the methods of the prior art because of the small quantity of the substances in the fingerprint.

The present invention provides, in a first aspect, a particle for use in a fluorescence detection method of a substance, the particle comprising a metal or a metal oxide, wherein one or more antibodies for binding to a substance is/are bound, directly or indirectly, to the surface of the metal or metal oxide. Preferably, the or each antibody is bound to the surface of the metal or metal oxide via Protein A or protein G, or any other protein and/or chemical linker, such as a thiolate linkage, which configures the antibody such that it is available to bind with the substance to be detected.

The present invention provides, in a second aspect, a method for making the particles of the present invention, the method comprising reacting particles comprising a metal or a metal oxide with an antibody to allow binding of the antibody to the particle. The particles may each comprise one or more Protein A's and/or Protein G's bound to the surface of the metal or metal oxide.

The present invention provides, in a third aspect, a method for the fluorescent detection of a substance, the method comprising providing particles comprising a metal or a metal oxide, wherein one or more antibodies for binding to a substance is/are bound, directly or indirectly, to the surface of the metal or metal oxide;

contacting a substrate, which may or may not have the substance on its surface, with the particles for a time sufficient to allow the antibody to bind with the substance;

removing those particles which have not bound to the substrate; and contacting the substrate with one or more fluorophores that selectively bind with the antibody and/or substance. The substrate is then preferably washed to remove fluorophores which do bind with the antibody and/or substance. The substrate is then illuminated with a source of appropriate radiation (e.g. visible or UV light) to show the fluorophores on the substrate.

The present invention provides, in a fourth aspect, a formulation containing particles for use in a fluorescence detection method of a substance, the particles comprising a metal or a metal oxide, wherein one or more antibodies for binding to a substance is/are bound, directly or indirectly, to the surface of the metal or metal oxide. The formulation may comprise the particles in powdered form. Alternatively, the formulation may be a liquid formulation containing the particles in a suspension. The formulation in powdered form may be created by freeze-drying the liquid suspension.

The present invention provides, in a fifth aspect, a kit for the fluorescent detection of a substrate, wherein the kit comprises (i) a liquid formulation containing a liquid containing as a suspension, particles for use in a fluorescent detection method of a substance, the particles comprising a metal or a metal oxide, wherein one or more antibodies for binding to a substance is/are bound, directly or indirectly, to the surface of the metal or metal oxide, and (ii) one or more fluorophores that selectively bind to the antibody and/or substance.

The particles comprise a metal or a metal oxide. Preferably, the particles comprise gold. The particles may be gold particles or the particles may comprise a core, optionally comprising iron oxide ($Fe_3O_4$ and/or $Fe_2O_3$), having a layer of metal thereon. The layer of metal may include one or more of gold, silver, platinum and copper.

The particles preferably have a diameter of less than 1 μm, more preferably less than 100 nm, most preferably less than 30 nm. The particles will be termed nanoparticles from hereon.

Metal and metal oxide nanoparticles may be synthesised and coated with monoclonal and/or polyclonal antibodies specific to each substance of interest, e.g. the target biological fluid. The resultant particle having a metal and/or metal oxide bound to an antibody may be termed an antibody-nanoparticle conjugate. Each antibody may then be tagged with individual or multiple fluorophores to enable differentiation of the target fluid. The antibody-nanoparticle conjugates may be used in the detection and differentiation of blood, semen and salvia, and in the detection of DNA and other substances of interest. The particles will act as solid supports for the antibodies. The nanometer size of the particles provides a large surface area and hence a high concentration of the antibody on the particle surface. This will provide multiple binding sites for the target species thereby increasing the sensitivity of fluorescence detection.

The present inventors have found that they are able to create monolayer structures surrounding particles of nanoscale dimensions (4-100 nm) based on self-assembly techniques. The particles can be created in aqueous solution and form a stable suspension. For the deposition of antibodies it is necessary to fabricate the antibody-nanoparticle conjugates using aqueous solutions to prevent denaturation of the biomolecule.

The particles may be or may comprise gold nanoparticles. The classical approach for the fabrication of aqueous based gold nanoparticles is that reported by Turkevich[1]. As described in Turkevich, the gold nanoparticles may formed through the citrate reduction of $HAuCl_4$. Importantly, the citrate not only reduces the metal salt but also acts as a capping agent stabilising the particles and preventing aggregation. Additionally, the citrate layer is readily displaced when a ligand containing a thiol/disulfide moiety is added to a solution of the particles. Fluorescently tagged antibodies will be deposited on the particles using either chemical or protein ligands to facilitate the formation of monolayers on the nanoparticle surface.

Figure 1:
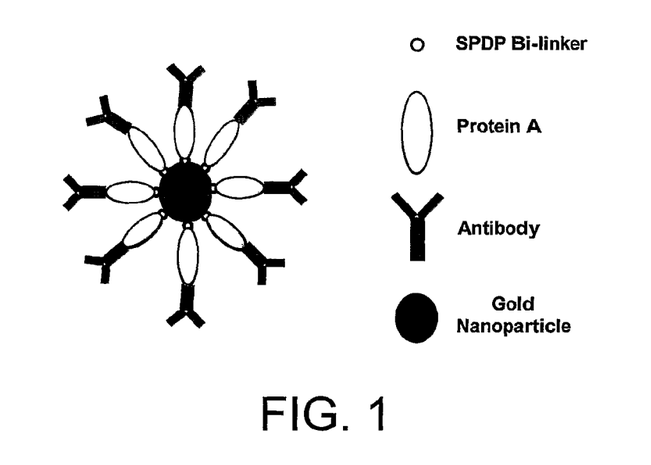
FIG. 1 shows a schematic representation of one embodiment of the antibody-nanoparticle conjugates. The conjugates are formulated by depositing a self-assembled monolayer of Protein A which acts as a biological linker to reproducibly orientate the anti-cotinine antibody on the gold particle surface.

As shown in the Example below, the present inventors have devised a simple, robust method for the formation of a monolayer of antibody using a protein linker to coat the surface of gold nanoparticles—the construction of the antibody-nanoparticle conjugates is schematically shown in FIG. 1. Gold nanoparticles of 16 nm diameter, formulated and stabilised using the citrate approach, were coated with a monolayer of Protein A. Protein A is a cell wall component of *Staphylococcus aureus* which specifically binds the Fc portion of an antibody (stalk of the Y). By binding the Fc component, the antibody is positioned such that the recognition component, the $F(ab')_2$ binding region (the top of the Y), is directly available to bind to the specific targeted antigen of the biological fluid. In order to form a monolayer of Protein A on the gold particle surface, the protein is first modified with N-succinimidyl 3-(2-pyridyldithio)-propionate (SPDP):—the succinimidyl ester binds the linker to a primary amine on the protein surface while the thiol moiety provides a linkage to the particle by displacing the citrate layer on the gold surface[2]. Once formed, the Protein A monolayer provides a surface to which the antibody binds such that the $F(ab')_2$ recognition component can directly, and reproducibly, bind to the antigen (the substance of interest). Protein A may be replaced by Protein G or a chemical linker, such as a thiolated linkage.

Protein A orientates the antibody for optimal presentation for antigen binding capability.

Alternatively, a simple chemically linked antibody on the nanoparticle may suffice, i.e. an antibody directly linked to the surface of the metal or metal oxide surface of the nano particle. A chemical linker, such as SPDP, may be attached to the antibody and allow direct attachment of the antibody to the metal, e.g. gold, or metal oxide. It is expected that an antibody bound to the particle using such linkers would be randomly orientated on the surface, potentially reducing binding affinity to the target. However, the advantage of the direct linkage is the ease of manufacture of these antibody-nanoparticle conjugates.

Antibodies that could be used for the detection of blood, semen and saliva in the present invention include, but are not limited to, (i) the anti-human secretory IgA or anti-proline rich protein 1 or 2 for saliva, both of which are found to be highly concentrated; (ii) anti-cytokeratin 13, which can be used to stain for buccal epithelial cells as a source of DNA; (iii) the erythrocyte membrane protein glycophorin (anti-CD235a), which can be used to stain for red blood cells and anti-human serum albumin (iv) anti-CD45 or an anti-neutrophil cytoplasmic antibody (ANCA), optionally selected from (i) p-ANCA (myeloperoxidase) and (ii) c-ANCA (proteinase 3 (PR3)), which can be used to stain for white blood cells as a source of DNA; (v) Sperm surface protein (anti-SP17 or SP56) and/or as well as prostrate specific antigen, which can be used to stain for semen. These antibodies are available commercially.

Methods for the attachment of an antibody to a metal or metal oxide core are disclosed herein. A particular example of the synthesis is shown in Example 1 for cotinine. In an analogous manner, other antibodies can be attached to metal/metal oxide cores by replacing cotinine with other antibodies.

Figure 7:
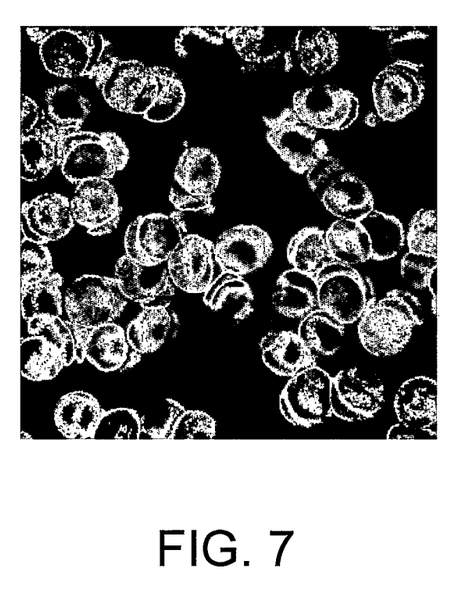
FIG. 7 shows blood dried on a coverslip, stained with anti-glycophorin antibody (primary) followed by anti-mouse FITC labelled secondary antibody.

Fluorescence microscopy data, produced by the present inventors, using erythrocyte membrane protein glycophorin for the detection of dried blood is shown in FIG. 7. This Figure demonstrates that dried stains can be visualised using the types of immunofluorescence approaches that can be employed in the method of the present invention. The present inventors have found that one should select antibodies which target surface membranes or extracellular components as our work has shown that in biological stains the cell membranes-remain in tact.

Fluorophores may be selected with consideration of: excitation and emission spectra relative to light sources routinely used in forensic science; the requirement for colour-mapping; sensitivity and substrate fluorescence.

Light sources used for evidence examination include: lasers; high intensity Xe and Hg arc lamps; and LED devices.

In order to simultaneously detect and spatially locate blood, semen, saliva and associated DNA in situ preferably multi-colour labelling techniques are used, i.e., a detection solution (the formulation of the present invention) containing the antibody-nanoparticle conjugates will be used with fluorophores which can be differentiated through non-overlapping emission bands when bound to their target biological matrix[3-5]. In other words, a fluorophore for the detection of blood will have different emission band from the fluorophore for the detection of semen, and likewise for saliva and DNA.

Fluorophores with emission spectra in the range ca. 430-650 nm are preferred and are commercially available. There are nine dyes in the Alexa Fluor range (Molecular Probes) within this wavelength "window", all of which exhibit exceptional photostability. These fluorophores are all water-soluble and possess a succinimidyl ester moiety enabling simple chemistries for tagging the antibodies via primary amine residues. Selection and evaluation of the fluorophores will take into account light sources currently used in forensic laboratories (excitation and emission wavelengths and bandwidth in relation to the ability to enable multi-colour mapping) and excitation and emission spectra of fluorescent substrates commonly encountered in forensic science[6-8].

The fluorophore may be fluorescent molecule attached (or tagged) to an F(ab')$_2$ fragment of a monoclonal antibody, preferably F(ab)$_2$ fragment of goat antimouse IgG.

Substrates that may be tested using the detection process of the present invention include, but are not limited to, paper, glass, plastic, wood, metal, cloth. Examples of such substrates include, but are not limited to, documents, wallpaper, sheets and clothing.

There are well-established methodologies for detection of DNA in solution but not for DNA in the dried state, as it often occurs in blood, semen or saliva stains. The present inventors have developed a method for the detection of DNA in its dried state. Two methods may be used:

The first approach employs the particles of the present invention in the methods as described herein, wherein the antibody can target DNA binding proteins such as Histone 1. Antibodies to Histone H1 are known in the art.

The second approach employs the particles of the present invention in the methods as described herein, wherein the antibody is replaced with human specific peptide nucleic acid (PNA) oligomers. The PNA oligomers will be custom synthesised (Eurogentec S.A.) to hybridise to Alu sequences (a family of interspersed nuclear repeat elements so called because they are recognised by the restriction endonuclease Alu1, they are scattered throughout the genome and account for about 5-10% of the total genome). The bases in PNA molecules are capable of Watson and Crick base pairing with DNA bases. Consequently, they have been used in fluorescence in situ hybridisation experiments[9] and can target DNA in live cells[10] where DNA is in its native configuration packaged into chromatin.

The PNA oligomers have also been found to bind in a sequence specific manner to the DNA found in biological stains. The PNA oligomers may be tagged with an appropriate fluorophore and then bound to nanoparticles and the resultant nanoparticle-DNA oligomer conjugates assessed for their binding to genomic DNA initially in cell suspensions and then in dried body fluids. One may lyse cells in body fluid stains to enable access of the antibody or PNA oligomers to DNA before or during contact with the particles of the present invention.

At the nanoscale particles of iron oxide (both $Fe_3O_4$ and $Fe_2O_3$) are superparamagnetic, i.e., they are attracted to a magnetic field but retain no residual magnetism after the field has been removed. This property may be utilised knowing that when a suspension of nanoparticles of the present invention is applied to a forensic sample, the antibody conjugates would bind to the target species; however those particles not bound could be readily removed using a simple magnet. Once the field is removed the bound particles would no longer be magnetic.

As is known to the skilled person, iron oxide nanoparticles are readily synthesised by the combination of $Fe^{2+}+Fe^{3+}$ salts in an alkaline solution under an atmosphere of nitrogen. The particles can then be stabilised using a variety of functionalised ligands. However, the pH of such a solution is too alkaline for the particles of the present invention, as the antibody would denature. Therefore rather than directly synthesising iron oxide particles one can synthesize particles having an iron oxide core with a gold shell or coating (termed FeAU nanoparticles), preferably using methods previously reported[11,12]. The FeAu nanoparticles retain the superparamagnetic properties of iron oxide particles but have the added advantage of the gold surface which can be used to formulate a reproducible self-assembled monolayer. The FeAu nanoparticles are synthesised in reverse micelles and then stabilised with a preferred ligand.

The particles of the present invention may comprise gold shell/iron oxide core nanoparticles, stabilised with a monolayer of antibody. The formulation of the present invention preferably contains the particles as a stable suspension and most preferably the particles are monodisperse i.e. of approximately the same size and, optionally, of the same kind.

The FeAu particles may be stabilised in a liquid using decanoic acid. A place rearrangement reaction in which the carboxylic acid is preferentially replaced by a thiolated ligand enables deposition of the chosen entity (as the SH moiety has a greater affinity for the gold surface). Previous approaches have used this technique to deposit fluorescent macrocycles on the surface of FeAu nanoparticles (the macrocycles retain their fluorescence properties following deposition). While, to the present inventors' knowledge, biomolecules have not been formulated on such nanoparticles. The various fluorescently tagged antibodies (and PNA oligomers) may be attached to the FeAu surface via direct chemical or Protein A (thiolated) linkers.

The formulation of the present invention may be applied by brushing or spraying the formulation onto the surface of the substrate. The brushes used may be magnetic brushes, e.g. those used for applying magnetic fingerprint powder.

The method of the present invention may be used to detect any substance for which there is a known antibody. The antibody may selectively bind to a drug, drug metabolite, hormone or explosive. For instance, one can use nanoparticles conjugated with drug, drug metabolite, hormone and explosives-specific monoclonal antibodies (specific to e.g. cocaine; benzoyl ecgonine; nicotine; cotinine, testosterone, oestrogen, TNT and RDX). Such antibodies are commercially available. The nanoparticle-antibody conjugates may be applied to body fluid stains and/or fingerprints known to contain the target substance. The sweat may be deposited on a substrate by means such as a taking a fingerprint from the subject. By testing for drugs or their metabolites in the sweat/body fluid stains, it is possible to determine whether a drug has been ingested by the subject, or simply handled. If a drug has been ingested by a subject, the drug and/or its metabolite will be present in a subject's excreted sweat/body fluid stains. However, if the drug had been handled, but not ingested, the drug may be present on a subject's skin, and may be transferred to, for example, the subject's fingerprint.

Drugs that may be detected using the method of the present invention, if suitable antibodies are available, include, but are not limited to:

A. ANABOLIC AGENTS. These include, but are not limited to:
1. Anabolic Androgenic Steroids (AAS)
a. Exogenous* AAS, including:
1-androstendiol (5α-androst-1-ene-3β,17β-diol); 1-androstendione (5α-androst-1-ene-3,17-dione); bolandiol (19-norandrostenediol); bolasterone; boldenone; boldione (androsta-1,4-diene-3,17-dione); calusterone; clostebol; danazol (17α-ethynyl-17β-hydroxyandrost-4-eno[2,3-d]isoxazole); dehydrochlormethyltestosterone (4-chloro-17β-hydroxy-17α-methylandrosta-1,4-dien-3-one); desoxymethyltestosterone (17α-methyl-5α-androst-2-en-17β-ol); drostanolone; ethylestrenol (19-nor-17α-pregn-4-en-17-ol); fluoxymesterone; formebolone; furazabol (17β-hydroxy-17α-methyl-5α-androstano[2,3-c]-furazan); gestrinone; 4-hydroxytestosterone (4,17β-dihydroxyandrost-4-en-3-one); mestanolone; mesterolone; metenolone; methandienone (17β-hydroxy-17α-methylandrosta-1,4-dien-3-one); methandriol; methasterone (2α,17α-dimethyl-5α-androstane-3-one-17β-ol); methyldienolone (17β-hydroxy-17α-methylestra-4,9-dien-3-one); methyl-1-testosterone (17β-hydroxy-17α-methyl-5α-androst-1-en-3-one); methylnortestosterone (17β-hydroxy-17α-methylestr-4-en-3-one); methyltrienolone (17β-hydroxy-17α-methylestra-4,9,11-trien-3-one); methyltestosterone; mibolerone; nandrolone; 19-norandrostenedione (estr-4-ene-3,17-dione); norboletone; norclostebol; norethandrolone; oxabolone; oxandrolone; oxymesterone; oxymetholone; prostanozol ([3,2-c]pyrazole-5α-etioallocholane-17β-tetrahydropyranol); quinbolone; stanozolol; stenbolone; 1-testosterone (17β-hydroxy-5α-androst-1-en-3-one); tetrahydrogestrinone (18a-homo-pregna-4,9,11-trien-17β-ol-3-one); trenbolone, and other substances with a similar chemical structure or similar biological effect(s).

b. Endogenous** AAS:

androstenediol (androst-5-ene-3β,17β-diol); androstenedione (androst-4-ene-3,17-dione); dihydrotestosterone (17β-hydroxy-5α-androstan-3-one) prasterone (dehydroepiandrosterone, DHEA); testosterone and the following metabolites and isomers: 5α-androstane-3α,17α-diol; 5α-androstane-3α,17β-diol; 5α-androstane-3β,17α-diol; 5α-androstane-3β,17β-diol; androst-4-ene-3α,17α-diol; androst-4-ene-3α,17β-diol; androst-4-ene-3β,17β-diol; androst-5-ene-3α,17α-diol; androst-5-ene-3α,17β-diol; androst-5-ene-3β,17α-diol; 4-androstenediol (androst-4-ene-3β,17β-diol); 5-androstenedione (androst-5-ene-3,17-dione); epi-dihydrotestosterone; 3α-hydroxy-5α-androstan-17-one; 3β-hydroxy-5α-androstan-17-one; 19-norandrosterone; 19-noretiocholanolone.

* "exogenous" refers to a substance which is not ordinarily capable of being produced by the body naturally.
** "endogenous" refers to a substance which is capable of being produced by the body naturally.

2. Other Anabolic Agents. These include, but are not limited to:

Clenbuterol, tibolone, zeranol, zilpaterol.

B. Hormones. These include, but are not limited to:
1. Erythropoietin (EPO);
2. Growth Hormone (hGH), Insulin-like Growth Factors (e.g. IGF-1), Mechano Growth Factors (MGFs);
3. Gonadotrophins (LH, hCG), prohibited in males only;
4. Insulin;
5. Corticotrophins.

C. BETA-2 AGONISTS, including their D- and L-isomers.

D. AGENTS WITH ANTI-ESTROGENIC ACTIVITY. These include, but are not limited to:
1. Aromatase inhibitors including, but not limited to, anastrozole, letrozole, aminoglutethimide, exemestane, formestane, testolactone
2. Selective Estrogen Receptor Modulators (SERMs) including, but not limited to, raloxifene, tamoxifen, toremifene.
3. Other anti-estrogenic substances including, but not limited to, clomiphene, cyclofenil, fulvestrant.

E. DIURETICS AND OTHER MASKING AGENTS. These include, but are not limited to:

Diuretics*, epitestosterone, probenecid, alpha-reductase inhibitors (e.g. finasteride, dutasteride), plasma expanders (e.g. albumin, dextran, hydroxyethyl starch) and other substances with similar biological effect(s).

Diuretics include:

acetazolamide, amiloride, bumetanide, canrenone, chlorthalidone, etacrynic acid, furosemide, indapamide, metolazone, spironolactone, thiazides (e.g. bendroflumethiazide, chlorothiazide, hydrochlorothiazide), triamterene, and other substances with a similar chemical structure or similar biological effect(s)

F. AGENTS FOR THE ENHANCEMENT OF OXYGEN TRANSFER. These include, but are not limited to:
1. Autologous, homologous or heterologous blood or red blood cell products of any origin.
2. perfluorochemicals, efaproxiral (RSR13) and modified haemoglobin products (e.g. haemoglobin-based blood substitutes, microencapsulated haemoglobin products).

G. STIMULANTS (including both their (D- & L-) optical isomers where relevant). These include, but are not limited to:

Adrafinil, adrenaline, amfepramone, amiphenazole, amphetamine, amphetaminil, benzphetamine, benzylpiperazine, bromantan, cathine*, clobenzorex, cocaine, cropropamide, crotetamide, cyclazodone, dimethylamphetamine, ephedrine**, etamivan, etilamphetamine, etilefrine, famprofazone, fenbutrazate, fencamfamin, fencamine, fenetylline, fenfluramine, fenproporex, furfenorex, heptaminol, isometheptene, levmethamfetamine, meclofenoxate, mefenorex, mephentermine, mesocarb, methamphetamine (β-), methylenedioxyamphetamine, methylenedioxymethamphetamine, pmethylamphetamine, methylephedrine**, methylphenidate, modafinil, niketamide, norfenefrine, norfenfluramine, octopamine, ortetamine, oxilofrine, parahydroxyamphetamine, pemoline, pentetrazol, phendimetrazine, phenmetrazine, phenpromethamine, phentermine, 4-phenylpiracetam (carphedon), prolintane, propylhexedrine, selegiline, sibutramine, strychnine, tuaminoheptane and other substances with a similar chemical structure or similar biological effect(s).

H. NARCOTICS These include, but are not limited to: buprenorphine, dextromoramide, diamorphine (heroin), fentanyl and its derivatives, hydromorphone, methadone, morphine, oxycodone, oxymorphone, pentazocine, pethidine.

I. CANNABINOIDS These include, but are not limited to: hashish, marijuana

J. GLUCOCORTICOSTEROIDS

K. ALCOHOL (ethanol)

L. BETA-BLOCKERS These include, but are not limited to:

acebutolol, alprenolol, atenolol, betaxolol, bisoprolol, bunolol, carteolol, carvedilol, celiprolol, esmolol, labetalol, levobunolol, metipranolol, metoprolol, nadolol, oxprenolol, pindolol, propranolol, sotalol, timolol.

M. AMPHETAMINES. These include, but are not limited to:

methamphetamine and MDMA (3,4-methylenedioxy-N-methylamphetamine); LSD (lysergic acid diethylamide); PCP (Phencyclidine), ketamine and derivatives;

N. ALKALOIDS AND THEIR DERIVATIVES. These include, but are not limited to:

nicotine, cocaine, ephedrine, mescaline; opium alkaloids (opiods), including morphine, and semi-synthetic opoids such as diamorphine (heroin); tryptamine alkaloids such as dimethyltriptamine and alpha-methyltryptamine;

O. BENZODIAZEPINES. These include, but are not limited to:
Alprazolam, Diazepam, Lorazepam, Clonazepam, Temazepam, Oxazepam, Flunitrazepam, Triazolam, Chlordiazepoxide, Flurazepam, and Nitrazepam, and nonbenzodiazepines, including Imidazopyridines, Pyrazolopyrimidines, Cyclopyrrones.

P. GHB (gamma-Hydroxybutyric acid) and derivatives

The method of the present invention may be used to detect metabolites of the drugs mentioned above, for which antibodies are available. If an antibody for a particular target substance, such as a drug or its metabolite, is not available commercially, the person skilled in the art could readily raise such an antibody using known techniques.

The fluorescently tagged nanoparticle-antibody conjugates using antibodies which bind to hormones may be applied to substrates on which latent fingerprints are suspected to be present. Hormones are produced in the body by males and females and excreted in sweat. By testing for hormones fingerprints from males and females can be visualised.

As stated above, the present invention provides, in a second aspect, a method for making the particles of the present invention, the method comprising reacting particles comprising a metal or a metal oxide with an antibody to allow binding of the antibody to the particle. The particles may each comprise one or more Protein A's and/or Protein G's bound to the surface of the metal or metal oxide.

Antibodies for many drug/drug metabolites are commercially available.

The antibody used in the present invention may be an antibody for an explosive compound. Antibodies that have already been fully characterised for specificity to TNT and RDX and these may be used to detect these explosive residues.

It is also possible to use the method of the present invention to detect metabolites resulting from the diseases, such as HIV.

Figure 3:
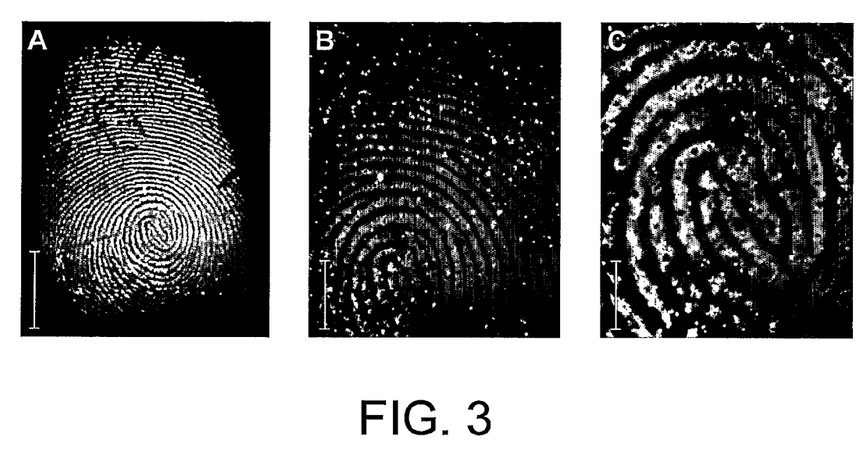
FIG. 3 shows fluorescence images, at varying magnifications, showing detailed fingerprint information. Images are taken from the thumb of a male smoker following 40 mins sweating using the anticotinine-nanoparticle conjugates illuminated using a secondary antibody (F(ab')$_2$ fragment of goat anti-mouse IgG tagged with Alexa Fluor 546). Scale bar represents: A, 5 mm; B, 2 mm; and C, 1 mm respectively.
Figure 4:
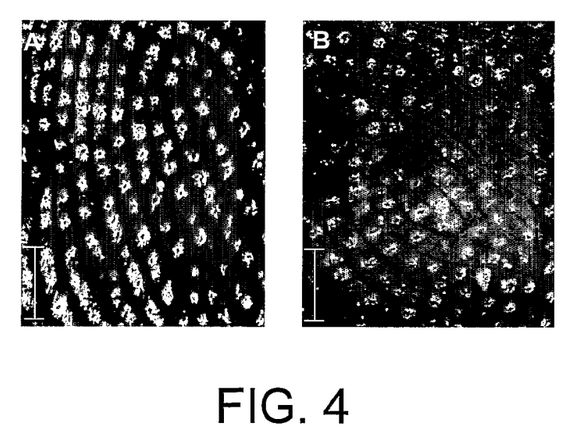
FIG. 4 shows higher magnification fluorescence fingerprint images showing high concentrations of cotinine exudate immediately surrounding the sweat pores. A—Middle finger of a male smoker following 10 minutes sweating; and B—Ring finger of a female smoker 'as presented'. Scale bars represent 1 mm.
Figure 5:
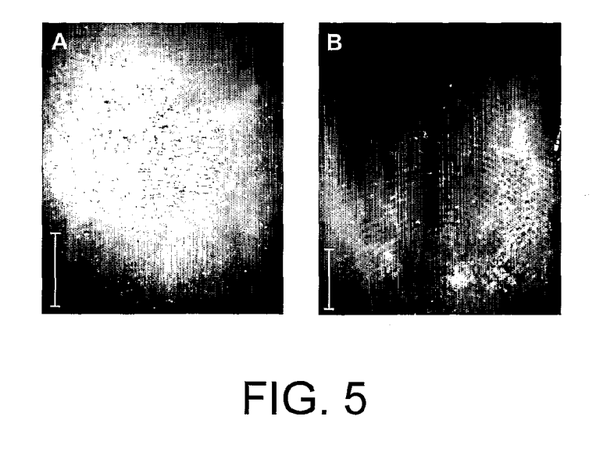
FIG. 5 shows fluorescence images taken from a male smoker following incubation with a solution of anti-cotinine antibody (Not structured on nanoparticles) and subsequently with (A) Alexa Fluor 488 and (B) Alexa Fluor 546 tagged F(ab')$_2$ fragment of goat anti-mouse IgG. Images taken of (A) little finger and (B) index finger. Scale bars represent 5 mm.
Figure 6:
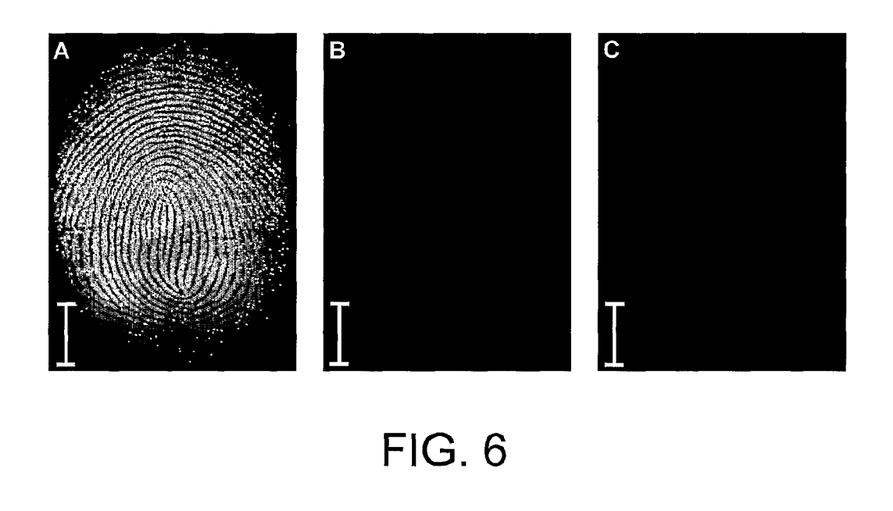
FIG. 6 shows the results of a control experiment of a (male) non-smokers' fingerprint. (A) shows a Brightfield image of an index finger. (B-C) are images obtained with the anti-cotinine-nanoparticle conjugates using the Alexa Fluor 488 and Alexa Fluor 546 tagged F(ab')$_2$ fragment of goat anti-mouse IgG, respectively showing no fluorescence. (B) Middle finger and (C) Index finger. Scale bars represent 5 mm.

As shown in the Example, one can attach an antibody for cotinine (the major metabolite of nicotine) to the surface of gold nanoparticles as schematically shown in FIG. 1. These antibody-nanoparticle conjugates can be used to detect cotinine in the latent fingerprints of a smoker. The cotinine antibody was bound to the particles and then incubated on the surface of the fingerprint. Excess nanoparticle solution was washed from the fingerprint surface. A fluorescently tagged (alexa fluor 546) secondary F(ab')$_2$ fragment antibody was then bound to the cotinine-nanoparticle conjugate. Again excess reagent was washed from the surface. The nanoparticle bound fingerprints were imaged using a fluorescence stereomicroscope—the image obtained is shown in FIG. 3. No fluorescence image was obtained from fingerprints of non-smokers.

This experiment shows that our antibody-nanoparticle detection strategy is capable of providing fluorescence information on the presence of a target species from latent fingerprints.

One may use a fluorescently tagged antibody, rather than attaching a separate fluorophore, such as a secondary antibody. One may also use FeAu nanoparticles in place of gold nanoparticles for the removal of non-bound particles. By employing these two techniques, the whole forensic procedure could therefore be carried out non-destructively (i.e. without washing) in situ and with improved sensitivity.

In a preferred embodiment, the present invention provides nanoparticles of from 4 to 100 nm having a gold surface and, optionally, a core comprising iron oxide, wherein one or more Protein A's and/or Protein G's are attached to the gold surface via thiolate linkage and an antibody is attached via a non-binding portion to the Protein A and/or G.

Protein A is a cell wall component of *staphylococcus aureus* that binds specifically to immunoglobulin molecules.

Protein A or Protein G is preferably attached to the gold surface by a thiolate linkage as shown between [Protein A/G] and [gold surface] as follows:

[Protein A/G]-NH—CO—(CH$_2$)$_n$—S-[gold surface], wherein n is 1 to 5, preferably 2, and NH is part of Protein A.

To synthesize the particles having a metal/metal oxide core bound to protein A or G via a sulphur-containing linker, preferably particles comprising a metal or a metal oxide, optionally capped with citrate, are contacted with SPDP modified Protein A or Protein G. The method of making the particles of the present invention preferably involves contacting particles having a metal/metal oxide core bound to protein A or G via a sulphur-containing linker with an antibody. Preferably, the contacting is carried out in a liquid, preferably water.

Protein A or Protein G is preferably attached to the thiolate-linkage precursor by reaction of Protein A or G with N-succinimidyl 1-3(2-pyridylthio) propionate (SPDP).

Protein A or Protein G may be attached to the gold surface of the nanoparticles by contacting in solution for a sufficient time gold nanoparticles capped with citrate and the reaction product of Protein A or G with SPDP. Protein A or G, on contact with an antibody in solution, will bind to the non-binding portion of an antibody, preferably the F$_c$ component.

References for the description above:
1. B. V. Enüstün and J. Turkevich, *J. Am. Chem. Soc.*, 1963, 85, 3317-3324.
2. S. Ferretti, S. Paynter, D. A. Russell, K. E. Sapsford and D. J. Richardson, *Trends Anal. Chem.*, 2000, 19, 530-540.
3. H. Hutter, *J. Microsc.*, 2004, 215, 213-218.
4. M. Kagen (plus 14 others) *J. Clin. Lig. Ass.*, 2002, 25, 104-110.
5. M. Ogawa, K. Tani, A. Ochai, N. Yamaguchi and M. Nasu, *J. Appl. Microbiol.*, 2005, 98, 1101-1106.
6. R. Hooker, K. Creer and J. Brennan, *For. Sci. Intl.*, 1991, 51, 297-304.
7. J. Burt and E. Menzel, *J. For. Sci.*, 1985, 30, 364-370.
8. H. Kobus, E. Silenieks, and J. Scharnberg, *J. For. Sci.*, 2002, 47, 819-823.
9. G. Cutrona, E. M. Carpaneto, M. Ulivi, S. Roncella, O. Landt, M. Ferrarini and L. C. Boffa. *Nature Biotechnol.*, 2000, 18, 300-303.
10. I. E. Agerholm, S. Ziebe, B. Williams, C. Berg, D. G. Cruger, G. Bruun Petersen and S. Koluraa. *Hum. Reprod.*, 2005, 20, 1072-1077.
11. J. Lin, W. Zhou, A. Kumbhar, J. Wiemann, J. Fang, E. Carpenter, C. O'Connor, *J. Solid State Chem.*, 2001, 159, 26-31.

W. Zhou, E. Carpenter, J. Lin, A. Kumghar, J. Sims, C. O'Connor, *Eur. Physical J. D.* 2001, 16, 289-292.

The present invention further provides a method for the fluorescent detection of a substance, the method comprising providing one or more fluorescently tagged antibodies for binding to a component of bodily fluid, preferably blood;

contacting a substrate, which may or may not have the component on its surface, with the one or more antibodies for a time sufficient to allow the antibody to bind with the component;

removing the antibodies which have not bound to the substrate;

and illuminating the substrate with appropriate radiation to show the fluorophores on the substrate.

Preferably, the one or more antibodies are selected from erythrocyte membrane protein glycophorin (CD235a); human serum albumin; leucocyte common antigen (CD45); an anti-neutrophil cytoplasmic antibody (ANCA).

The ANCA is preferably selected from (i) p-ANCA (myeloperoxidase); and (ii) c-ANCA (proteinase 3 (PR3)).

Preferably, the antibodies may be bound to one or more fluorophores via a succinimidyl ester moiety.

The present invention further provides a fluorescently tagged antibody for binding to a component of bodily fluid, preferably blood, wherein the antibody is selected from erythrocyte membrane protein glycophorin (CD235a); human serum albumin; leucocyte common antigen (CD45); an anti-neutrophil cytoplasmic antibody (ANCA). The antibody is preferably bound to one or more fluorophores via a succinimidyl ester moiety.

The fluorescently tagged antibodies can be synthesised by contacting a fluorophore for attachment to an antibody with the antibody, preferably in solution. A linking compound may be present for linking the antibody to the fluorophore moiety, the linking compound preferably comprising succinimidyl ester. The fluorophore may be selected from any suitable fluorophore available to the skilled person.

The present invention will now be illustrated in the following non-limiting Examples and with reference to the following drawings, in which.

EXAMPLE 1

The present inventors have devised a simple, yet robust, method for the formation of antibody-functionalised nanoparticles using a self-assembled monolayer (SAM) of a protein linker to coat the surface of gold nanoparticles. Gold nanoparticles of 16 nm diameter, were formulated using the Turkevich approach (B. V. Enüstün and J. Turkevich, *J. Am. Chem. Soc.*, 1963, 85, 3317-3324) which uses citrate as both a reductant and a stabilizing agent. Referring to FIG. 1, Protein A—a cell wall component of *Staphylococcus aureus*—was first modified with N-succinimidyl 3-(2-pyridyldithio)-propionate (SPDP) to enable the formation of a self-assembled monolayer (SAM) of the Protein A on the surface of gold nanoparticles (the succinimidyl ester binds the SPDP to a primary amine on the protein surface, while the thiol moiety provides a linkage to the gold surface (See: S. Ferretti, S. Paynter, D. A. Russell, K. E. Sapsford and D. J. Richardson, *Trends Anal. Chem.*, 20000, 19, 530-540)). A SAM of Protein A is formed upon addition of the SPDP-modified Protein A to the nanoparticles with the thiolated ligand displacing the citrate layer on the gold particle surface. Protein A was used as a linker as the protein specifically binds the Fc portion of an antibody (See: E. Harlow and D. Lane in Antibodies: A laboratory Manual (Eds. E. Harlow and D. Lane) Cold Spring Harbour Laboratory, New York, 1988, pp 616-621). By binding the Fc component, the Protein A orientates the antibody such that the recognition component, the F(ab')$_2$ binding region, is optimally presented for direct, and reproducible, antigen binding. Anti-cotinine was readily deposited onto the Protein A monolayer on the gold nanoparticles. However, it should be noted that this strategy can be applied to functionalise nanoparticles with numerous antibodies enabling detection of multiple specific antigens.

Figure 2:
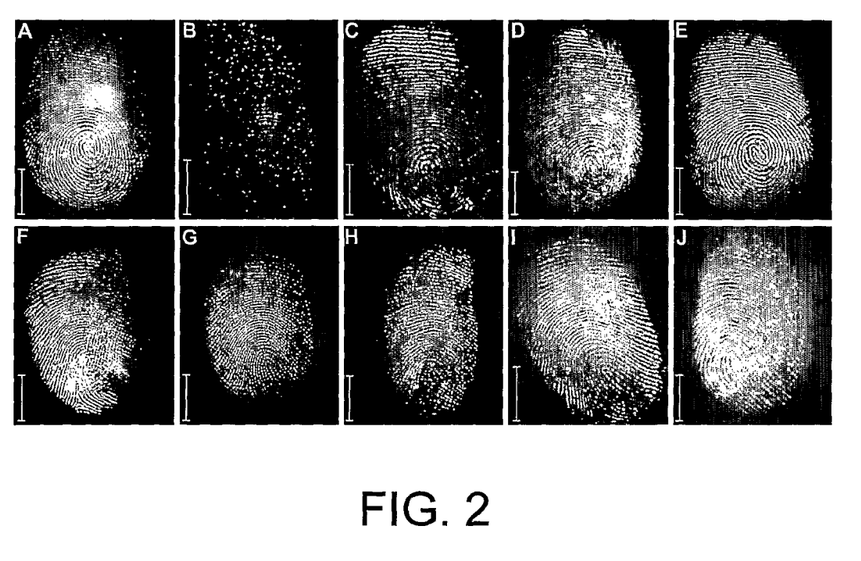
FIG. 2 shows the evolution of fingerprint development using anticotinine-nanoparticle conjugates. Fingerprints are from a male smoker—the fluorescence images are derived from a secondary antibody (F(ab')$_2$ fragment of goat anti-mouse IgG) tagged with either Alexa Fluor 546 (A to E) or Alexa Fluor 488 (F to J). Images A and F are fingerprints are taken from subject as presented; images B-E and G-J were taken after the subject washed his hands and then gave a fingerprint after a predetermined 'sweating' time—B and G (10 minutes), C and H (20 minutes), D and I (30 minutes) and E and J (40 minutes). Images A to E are taking from the thumb, F, G and I are images of the middle finger, H is an image of the index finger while J is an image of the little finger. In each instance the scale bar represents 5 mm.

The anti-cotinine functionalised nanoparticles were applied to the detection of cotinine in the fingerprints of smokers. In a typical experiment the volunteer smoker would provide a fingerprint (such fingerprints are described 'as presented'), then asked to wash their hands and then sweating was induced by placing the volunteer's hand in a sealed glass beaker. Fingerprints were then taken at regular intervals between 10-40 mins. The cotinine-nanoparticle conjugates were pipetted onto the fingerprints and incubated for 30 min. Following incubation the fingerprint was washed to remove unbound nanoparticle conjugates. A fluorescently tagged secondary antibody fragment (F(ab')$_2$ region) was then incubated and excess reagent then removed by washing with water. Fluorescence images were then taken of the fingerprints. FIG. 2 shows the fingerprint images obtained from a male smoker (reporting to smoke between 5-7 cigarettes p.d.) using 2 fluorescently labelled secondary antibody fragments.

Methods and Materials

Reagents:

All reagents were purchased from Sigma-Aldrich (Gillingham, UK) unless stated, were of analytical grade and used without any further purification. Milli-Q water was used throughout for solution preparation unless otherwise stated.

UV-Visible Absorption Measurements:

A Hitachi U3000 UV-visible spectrophotometer was used to record absorption spectra, at a temperature of 22° C.

Transmission Electron Microscopy (TEM):

To characterise the size and structure of the gold nanoparticles and following subsequent addition of Protein A, transmission electron microscopy (JEOL 2000EX operating at 100 kV) was used. A 5 µl drop of the nanoparticle sample was placed on a carbon coated 200 mesh copper grid. Excess liquid was removed by contacting the side of the grid with absorbent paper tissue and then allowing the grid to dry for a further 5 min.

Thiolation of Protein A:

To enable the self assembly of Protein A onto the gold nanoparticle surface, the heterobifunctional reagent N-succinimidyl 3-(2-pyridyldithio) propionate (SPDP) was used. SPDP (10 mM, 60 µl in ethanol (Fisher, Loughborough, UK)) was added to Protein A (5 µM, 2.5 ml in 100 mM phosphate buffer (Fisher, Loughborough, UK) pH 7.8) and stirred for 30 minutes. Unbound SPDP was removed using a Sephadex P-10 desalting column (Amersham Biosciences, Little Chalfont, UK). First the column was equilibrated with phosphate buffer (10 mM, pH 7.4) and then the Protein A-SPDP complex (2.5 ml) was added onto the column and bound SPDP-Protein A was eluted with phosphate buffer (10 mM pH 7.4).

Confirmation of Protein A Thiolation:

SPDP conjugation to Protein A was confirmed using DL-dithioreitol (DTT).[1] DTT specifically reduces the SPDP disulphide bond to give 2-thiopyridone, the oxidised form of DTT. This reaction can be monitored at 343 nm, the $\lambda_{max}$ of 2-thiopyridone (6343=8.08×10$^3$ M$^{-1}$ cm$^{-1}$), to confirm that SPDP was bound to Protein A. An initial UV-visible spectrum was taken of the SPDP-Protein A complex (0.1 ml made up to 1 ml with phosphate buffer 10 mM pH 7.4) and DTT (0.1 M, 25 µl in water) was added to the Protein A-SPDP solution and UV-visible spectrum taken 30 minutes after addition of DTT.

Synthesis of Gold Nanoparticles:

Water soluble gold nanoparticles (3 nM) were prepared by the reaction of hydrogen tetrachloroaurate salt and the reducing and capping agent sodium citrate dihydrate (Fisher Loughborough, UK).[2] Sodium citrate dihydrate (50 mg, 50 ml water) and hydrogen tetrachloroaurate(III) trihydrate (12.5 mg, 100 ml in water, pale yellow) both solutions were heated to 60° C., then rapid addition of the citrate to the gold solution was followed by increasing the temperature to 85° C. for 2½ h with continuous stirring. The resulting solution was a deep red colour; characteristic of citrate stabilised gold nanoparticles of 16 nm diameter. The particle size was verified by transmission electron microscopy (TEM).

Synthesis of Protein A Modified Gold Nanoparticles:

SPDP modified Protein A (1.6 M) was added to gold nanoparticles (3 nM) and stirred continuously for 48 hours to assist self assembly. Protein A stabilised gold nanoparticles were centrifuged (Beckman Coulter Avanti™ J-25 centrifuge) at 53343×g and 4° C. for 30 minutes. The clear supernatant was pipetted off carefully, leaving a soft pellet (~0.5 ml) with a deep red colour and this was resuspended in phosphate buffer (10 mM, pH 7.4). The centrifugation process was repeated in triplicate to remove any unbound Protein A-SPDP. A UV-visible spectrum (800-300 nm) was taken of the final resuspended solution.

Addition of Anti-Cotinine to Protein A-Gold Complex:

IgG anti-cotinine (40 µl, 5.4 mg/ml (Europe Bioproducts Ltd., Ely, UK)) was added to the Protein A modified gold nanoparticles (20 ml) and stirred for 2½ h hours. The centrifugation process was repeated, leaving a soft deep red pellet (~0.5 ml) after the clear supernatant was removed and on the last resuspension 5 ml of phosphate buffer was used (10 mM, pH 7.4). A UV-visible spectrum (800-300 nm) was taken of the final resuspended solution.

Brightfield and Fluorescent Microscopy:

Brightfield and fluorescent images of latent fingerprints were acquired using a Zeiss M2 Bio Quad SV11 stereomicroscope. The fingerprints were illuminated either with a halogen lamp (brightfield) or a 100 W Hg arc lamp (fluorescence), and reflected-light images captured with an AxioCam HRc CCD camera and Axio Vision software (Carl Zeiss, Welwyn Garden City, UK). Alexa Fluor 488® (Invitrogen, Paisley, UK) was excited with light passed through a 470 nm filter (40 nm bandpass) and the emission collected through a 525 nm filter (50 nm bandpass). Alexa Fluor 546® (Invitrogen, Paisley, UK) was excited using a 560 nm excitation filter (40 nm bandpass) and a 630 nm emission filter (60 nm bandpass).

Imaging of Cotinine on Latent Fingerprints using Anti-Cotinine Gold Complex:

Glass slides were cleaned thoroughly using lint free Kimwipes® and methanol (HPLC grade) to remove the contamination on the slide. A lens cleaning tissue was placed on top of the glass slide, then glass cleaning fluid (6 µl) (Wizz Products LtD, Leeds, UK) was applied across the tissue at top the slide and the tissue was dragged across the slide to remove any dust and/or smears on the slide. This last step was then completed for the underside of the slide. A smoker/non smokers fingerprint was then applied to the slide and then brightfield images taken. To contain the anti-cotinine gold complex on the fingerprint surface a hydrophobic barrier was applied around the fingerprint using an ImmEdge hydrophobic barrier pen (Vector, Peterborough, UK) to contain a liquid on the fingerprint. A fresh batch (used within 1 day of production) of anti-cotinine-gold complex (~200 µl) was carefully applied to the fingerprint and the slide was incubated for 30 minutes at 37° C. in a wet chamber (moist tissue around the glass slide in a plastic petri dish). The fingerprint area was then washed with water to remove unbound anti-cotinine-gold complex. Anti-mouse secondary antibody (F(ab')$_2$ Region), either tagged with Alexa Fluor 488 or 546 ((Invitrogen, Paisley, UK) 20 µl of a 1 in 20 dilution of stock) was added to the fingerprint area and incubated as for the primary antibody. The slide was again washed with water to remove any unbound secondary antibody and fluorescent images taken.

Imaging of Cotinine on Latent Fingerprints Using Anti-Cotinine:

The procedure for imaging cotinine on latent fingerprints was then repeated for a control sample of anti-cotinine. The anti cotinine (40 µl) was added to phosphate buffer (10 mM, pH 7.4, 5 ml) to give a stock solution. Brightfield images were taken of smokers and non-smokers latent fingerprints prior to incubation. Fluorescent images were taken of the latent fingerprints after incubation as described for the anti-cotinine gold complex.

References for the Example:
1) Imoto, T.; Yamada, H. In Protein Function—A Practical Approach; Creighton, T. E., Ed.; IRL Press: Oxford, 1997, pp 247-259.
2) Hone, D. C.; Haines, A. H; Russell, D. A.; Langmuir, 2003, 19, 7141-7144.

EXAMPLE 2

This example illustrates the use of certain antibodies in the detection of blood.

a) Antibody and Fluorophore Selection

In the following Example, monoclonal antibodies are directly labelled with specific fluorophores rather than indirect labelling which makes use of a 2° labelled antibody that is specific for the 1° antibody. This single antibody approach allows for faster analysis of dried blood stains as well as reducing the risk of cross reactivity that can occur using an indirect approach.

Alexa Fluor dyes, with the succinimidyl ester moiety for allowing the labelling of primary amine residues on the monoclonal antibodies, were selected due to their brightness, photostability, instrument compatibility, pH insensitivity and water solubility.

Commercially available monoclonal antibodies were selected on the basis of human cell type specificity. Leucocytes are naturally important targets within the blood smears due to the presence of nuclei and therefore, DNA which is absent from erythrocytes. It is also important to note that granulocytes (neutrophils, basophils and eosinophils) make up the majority of the white blood cell population, therefore these are seen as good target cells within a blood smear. The antibodies selected for were as follows:

1. Erythrocyte membrane protein glycophorin (CD235a)
2. Human serum albumin
3. Leucocyte common antigen (CD45)
4. Anti-neutrophil cytoplasmic antibodies (ANCA's):

i) p-ANCA (myeloperoxidase) which is typically located in the perinuclear region in granulocytes ii) c-ANCA (proteinase 3 (PR3)) which is typically located in the cytoplasm of granulocytes For the detection of DNA within a leucocyte population, histones (DNA binding proteins) were selected as targets. Histone H1 is viewed to be more varied between species than the more conserved H2A, H2B, H3 and H4, so this was selected as a target. The H1 subtype H1.3 was also selected as this should be human specific. However, the staining of these histones will not show cell specificity, so it is viewed that these antibodies will have to be used in conjunction with leucocyte specific antibodies such as CD45 or ANCA labelled with a different fluorophore.

b) Materials and Methods i) Antibody Labelling

Alexa fluor dyes (488, 568), carboxylic acid, succinimidyl ester 1 mg (Invitrogen) were dissolved in dimethylformamide (DMF) to a concentration of 1 mg/mL. The monoclonal antibodies were normally purchased in a solution of PBS and sodium azide without BSA or gelatin and at a concentration of at least 1 mg/mL. To 70 µL of antibody solution, NaHCO$_3$ (pH 8.5) was added to a final concentration of 100 mM. The dye was added at a ratio of 10:1 dye to protein and reacted for 1 hr (Alexa Fluor 488) or 2 hrs (Alexa Fluor 568) in the dark at room temperature with mixing every 15 minutes.

The unbound dye was removed using 0.5 mL Zeba desalt spin columns (Pierce) which typically showed 95% retention of salts and other molecules<1000 MW and high protein recovery (c. 90-95%). The protein concentration and the dye: protein ratio was measured using a Nano Drop and calculated as follows:

Protein Conc:

$$\frac{[A280 - [A568 \times \text{correction factor}]] \times \text{dilution factor}}{\varepsilon \text{ protein (203,000 for } IgG) \text{ cm} - 1M - 1}$$

Correction factor = dye absorbance at 280 nm (0.46 for $AF568$ & 0.11 for $AF488$ )

Degree of Labelling:

$$\frac{A568 \times \text{dilution factor}}{\varepsilon \text{ (dye) cm} - 1M - 1}$$

$\varepsilon$ for $AF488 = 71,000$ $\varepsilon$ for $AF568 = 91,300$

Typically a good labelling gave about 3 dye molecules: 1 molecule of protein, however, if it was under-labelled a fresh batch of dye was added and reacted for another 1 hour. Over-labelling caused fluorophore quenching or non-specific staining.

Sodium azide was added to a final concentration of 2 mM to act as a preservative.

ii) Cell Preparation

Human blood was smeared on adhesive slides (Surgipath), dried and fixed in MeOH for 10 mins at room temperature. This was followed by washing 2× in PBS (100 mM, pH 7.2) and further drying. The area to be labelled was defined with a PAP pen and the conjugated antibody (depending on concentration) was usually applied at 1:25 or 1:50 in PBS with 2.5% BSA for 30 minutes. Blood smears were then washed with PBS and mounted in anti-fluorescent medium (Dako).

Brightfield and fluorescent images were acquired on a Zeiss Axioskop 2 MOT plus stereomicroscope. Blood smears were illuminated with either a halogen lamp for brightfield, or a 100 W Hg arc lamp for fluorescence. Images were captured with an AxioCam HRC CCD camera and processed using Axiovision 3.1 software.

c) Images

FIGS. 8 to 12 show human erythrocytes, leucocytes and albumin directly stained with specific labeled antibodies.

Figure 8:
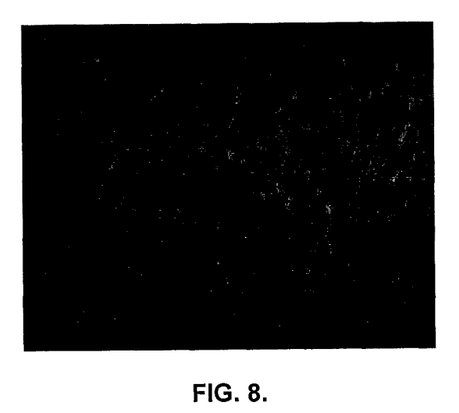
FIGS. 8 to 12 show human erythrocytes, leucocytes and albumin directly stained with specific labelled antibodies, as described in Example 2.

FIG. 8 shows human erythrocytes×400 from a dried blood smear labeled with rat anti-human CD235a Alexa Fluor 568.

Figure 9A:
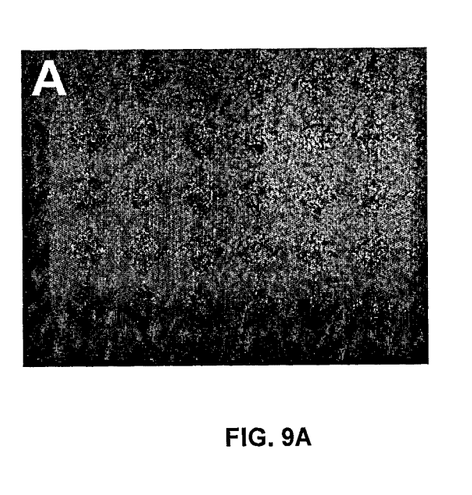
Figure 9B:
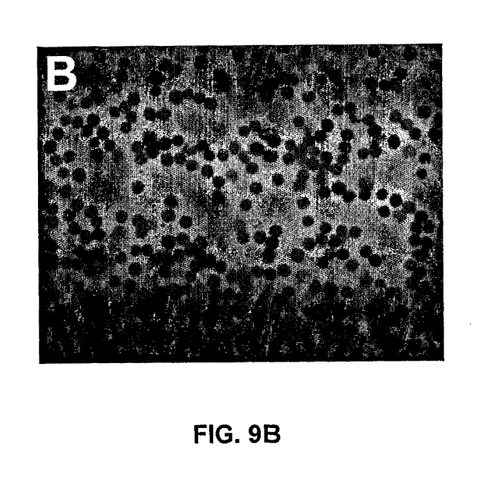

FIG. 9 shows human serum albumin from a human blood smear labeled with mouse anti-human albumin Alexa Fluor 488 (A)×100 (B)×400.

Figure 10A:
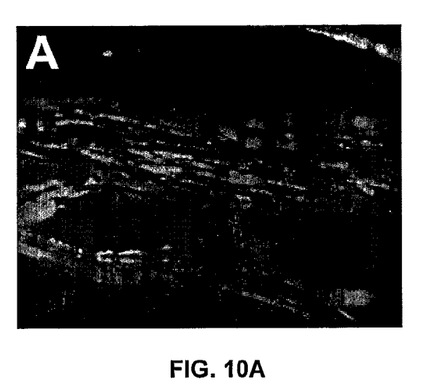
Figure 10B:
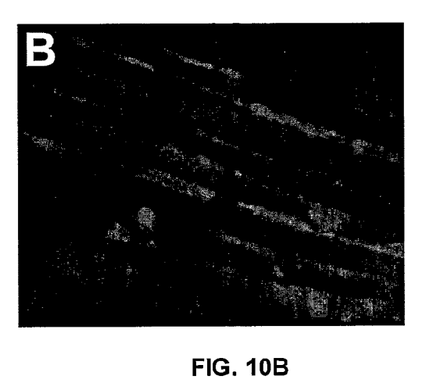

FIG. 10 shows two examples of dried human erythrocytes on black cotton×200 labeled with rat anti-human CD235a Alexa Fluor 568.

Figures 11A, 11B, 11C:
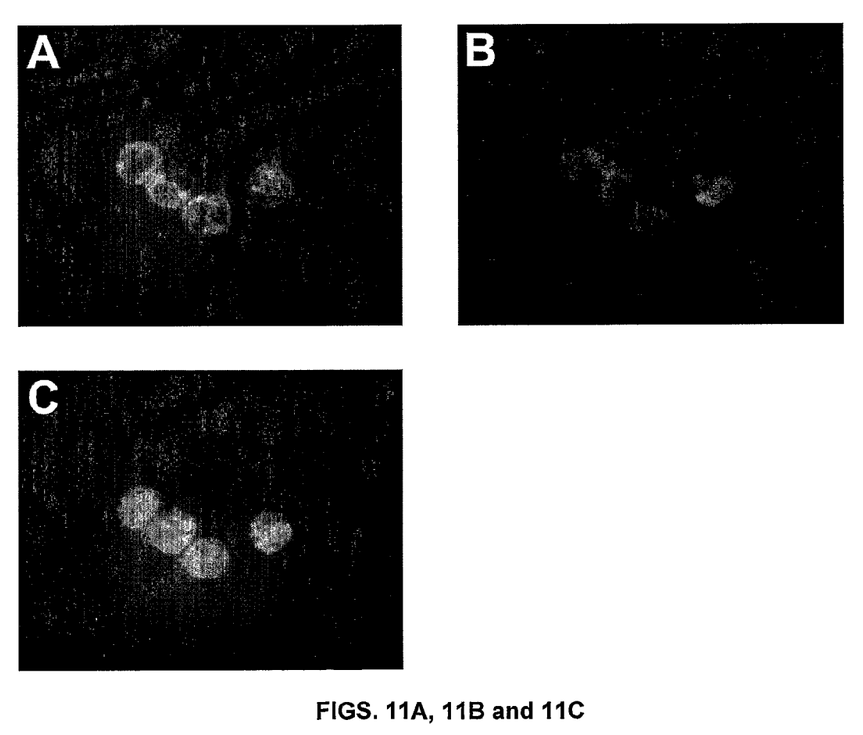

FIG. 11 shows human neutrophils×1000 from a dried blood smear labeled with (A) mouse anti-human CD45 Alexa Fluor 488 (B) mouse anti-human histone H1 Alexa Fluor 568 (C) overlay of images A & B.

Figure 12:
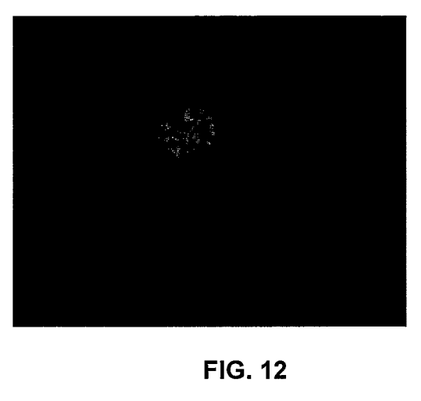

FIG. 12 shows human lymphocyte or monocyte×1000 from a dried blood smear labeled with rabbit anti-human histone H1.3 Alexa Fluor 568 d) Specificity

It was found that rat anti-human CD235a, mouse anti-human CD45 and mouse anti-human albumin showed no cross reactivity with dog, rabbit or pig blood. Mouse anti-human histone H1 showed cross reactivity with these three different blood types. However, it could still be used in conjunction with CD45 to show cell specificity and human specificity. This would provide a useful tool in detecting a blood stain and DNA directly.

Example 2 shows the effective use of certain antibodies in the detection of blood. The antibodies may be attached to metal or metal oxide-containing cores in an analogous manner to the method shown in Example 1.

The invention claimed is:

1. A method for the fluorescent detection of a substance, the method comprising:
   providing particles comprising a metal or a metal oxide core, wherein one or more optionally fluorescently tagged antibodies or human specific peptide nucleic acid (PNA) oligomers for binding to a substance is/are bound, directly or indirectly, to the surface of the metal or metal oxide;
   contacting a substrate, which may or may not have the substance on its surface, with the particles for a time sufficient to allow the antibody/PNA oligomer to bind with the substance;
   removing those particles which have not bound to the substrate;
   if the antibodies or PNA oligomers are not fluorescently tagged, contacting the substrate with one or more fluorophores that selectively bind with the antibody and/or substance, then optionally washing the substrate to remove unbound fluorophores; and
   illuminating the substrate with appropriate radiation to show the fluorophores on the substrate, wherein the substrate has a fingerprint of a human on a surface on which the particles are contacted.

2. The method according to claim 1, wherein the core comprises one or more metals selected from gold, silver, platinum and copper.

3. The method according to claim 1, wherein the core comprises an iron oxide.

4. The method according to claim 1, wherein the particles have a core comprising an iron oxide, the core having a layer of metal thereon, the metal being selected from gold, silver, platinum and copper.

5. The method according to claim 3, wherein the iron oxide is $Fe_3O_4$ or $Fe_2O_3$.

6. The method according to claim 1, wherein at least some of the cores of particles have a diameter of less than 100 nm.

7. The method according to claim 1, wherein the one or more antibodies or PNA oligomers are bound directly to the surface of the metal or metal oxide.

8. The method according to claim 1, wherein the one or more antibodies or PNA oligomers are bound to the surface of the metal or metal oxide via a sulphur-containing linker.

9. The method according to claim 1, wherein the one or more antibodies or PNA oligomers are bound to the surface of the metal or metal oxide via Protein A or Protein G.

10. The method according to claim 1, wherein the one or more antibodies or PNA oligomers are bound to the surface of the metal or metal oxide as follows:

[antibody or PNA oligomer]-[Protein A or G]-NH—CO—$(CH_2)_n$—S—

[metal or metal oxide surface],
wherein n is 1 to 5 and NH is part of Protein A or Protein G.

11. The method according to claim 1, wherein the one or more antibodies selectively bind to Histone H1, cocaine, benzoyl ecgonine, nicotine, cotinine, one or more steroids, TNT or RNX.

12. The method according to claim 1, wherein the one or more antibodies is selected from antibodies that selectively bind to human salivary amylase, prostate specific antigen, erythrocyte membrane protein glycophorin (CD235a), human serum albumin and leucocyte common antigen (CD45) or wherein the one or more antibodies is an anti-neutrophil cytoplasmic antibody (ANCA) optionally selected from (i) p-ANCA (myeloperoxidase) and (ii) c-ANCA (proteinase 3 (PR3)).

13. The method according to claim 1, wherein the fingerprint is a latent fingerprint.

14. The method according to claim 13, wherein the latent fingerprint is sweat deposited as an impression of a finger's ridge pattern.

* * * * *